United States Patent [19]

Dessau et al.

[11] Patent Number: 6,008,388
[45] Date of Patent: Dec. 28, 1999

[54] EPOXIDATION PROCESS

[75] Inventors: Ralph M. Dessau, Edison, N.J.; Andrew P. Kahn, Eagleville, Pa.; Roger A. Grey, West Chester, Pa.; C. Andrew Jones, Newtown Square, Pa.; Jennifer D. Jewson, Boyertown, Pa.

[73] Assignee: ARCO Chemical Technology, L.P., Greenville, Del.

[21] Appl. No.: 09/290,647

[22] Filed: Apr. 12, 1999

Related U.S. Application Data

[60] Provisional application No. 60/081,939, Apr. 16, 1998.
[51] Int. Cl.$^6$ .................... C07D 301/12; C07D 303/04
[52] U.S. Cl. ................................................. 549/531
[58] Field of Search ............................... 549/531

[56] References Cited

U.S. PATENT DOCUMENTS 4,410,501 10/1983 Taramasso et al. .................... 423/326
5,599,956 2/1997 Pujado et al. .......................... 549/531

FOREIGN PATENT DOCUMENTS 196 00 709   7/1997   Germany .
4-352771    12/1992   Japan .
H8 269029   10/1996   Japan .
H8269030    10/1996   Japan .

*Primary Examiner*—Ba K. Trinh
*Attorney, Agent, or Firm*—William C. Long

[57] ABSTRACT

The selectivity of an olefin epoxidation catalyzed by a noble metal-modified titanium or vanadium zeolite is greatly enhanced by the addition of a nitrogen compound to the reaction mixture. The epoxidation utilizes hydrogen and oxygen in addition to the olefin.

17 Claims, No Drawings

EPOXIDATION PROCESS

RELATED APPLICATION

This application claim the benefit of Provisional Application Ser. No. 60/081,939 filed Apr. 16, 1998.

FIELD OF THE INVENTION

This invention relates to methods of oxidizing olefins to obtain epoxides. More particularly, this invention pertains to an improved epoxidation process wherein a nitrogen-containing modifier such as ammonia or ammonium hydroxide is utilized to enhance the selectivity of a titanium zeolite catalyst which has been modified with a noble metal such as palladium. Use of these modifiers increases propylene oxide production, reduces by product formation and improves the $H_2/O_2$ utilization.

BACKGROUND OF THE INVENTION

Epoxides constitute an important class of chemical intermediates useful for the preparation of polyether polyols, glycols, glycol ethers, surfactants, functional fluids, fuel additives and the like. Many different methods for synthesizing epoxides from the corresponding olefins have been described in the literature. A Japanese patent application assigned to the Tosoh Corporation and published in 1992 (Kokai No. 4-352771) proposed making propylene oxide by reacting propylene, hydrogen and oxygen using a catalyst comprising a Group VIII metal and a crystalline titanosilicate. Improvements to or variations of this basic process were subsequently described in the following published patent applications: WO 97/25143, DE 19600709, WO 96/02323, WO 97/47386, WO 97/31711, JP H8-269030, and JP H8-269029.

As with any chemical process, it would be desirable to attain still further improvements in epoxidation methods of this type. In particular, increasing the selectivity to epoxide and extending the useful life of the catalyst would significantly enhance the commercial potential of such methods. Using the reaction conditions and catalysts described in the literature, for example, hydrogenation of the olefin to the corresponding saturated hydrocarbon competes with the desired epoxidation reaction. The discovery of more effective ways of suppressing this side-reaction would be highly advantageous.

SUMMARY OF THE INVENTION

This invention provides a process for producing an epoxide comprising reacting an olefin, hydrogen and oxygen in the presence of (a) a catalyst comprised of a titanium zeolite and a noble metal and (b) a nitrogen-compound modifier at a temperature effective to form the epoxide corresponding to the olefin.

DETAILED DESCRIPTION OF THE INVENTION

The catalysts to be used in the present process are comprised of a titanium or vanadium zeolite and a noble metal (preferably an element of Group VIII of the Periodic Table). Suitable zeolites are those crystalline materials having a porous molecular sieve structure with titanium or vanadium atoms substituted in the framework. The choice of zeolite employed will depend upon a number of factors, including the size and shape of the olefin to be epoxidized. For example, it is preferred to use a relatively small pore titanium or vanadium zeolite such as a titanium silicalite if the olefin is a lower aliphatic olefin such as ethylene, propylene, or 1-butene. Where the olefin is propylene, the use of a TS-1 titanium silicalite or vanadium silicalite is especially advantageous. For a bulky olefin such as cyclohexene, a larger pore titanium zeolite such as a titanium zeolite having a structure isomorphous with zeolite beta may be preferred.

The titanium-containing zeolites useful as catalysts in the epoxidation step of the process comprise the class of zeolitic substances wherein titanium atoms are substituted for a portion of the silicon atoms in the lattice framework of a molecular sieve. Such substances are well known in the art.

Particularly preferred titanium-containing zeolites include the class of molecular sieves commonly referred to as titanium silicalites, particularly "TS-1" (having an MFI topology analogous to that of the ZSM-5 aluminosilicate zeolites), "TS-2" (having an MEL topology analogous to that of the ZSM-11 aluminosilicate zeolites), and "TS-3" (as described in Belgian Pat. No. 1,001,038). Also suitable for use are the titanium-containing molecular sieves having framework structures isomorphous to zeolite beta, mordenite, ZSM-48, ZSM-12, and MCM-41. The titanium-containing zeolite preferably contains no elements other than titanium, silicon and oxygen in the lattice framework, although minor amounts of boron, iron, aluminum, and the like may be present. Other metals such as tin or vanadium may also be present in the lattice framework of the zeolite in addition to the titanium, as described in U.S. Pat. Nos. 5,780,654 and 5,744,619.

Preferred titanium-containing zeolite catalysts suitable for use in the process of this invention will generally have a composition corresponding to the following empirical formula $xTiO_2$ $(1-x)SiO_2$ where x is between 0.0001 and 0.500. More preferably, the value of x is from 0.01 to 0.125. The molar ratio of Si:Ti in the lattice framework of the zeolite is advantageously from 9.5:1 to 99:1 (most preferably from 9.5:1 to 60:1). The use of relatively titanium-rich zeolites may also be desirable.

While any of the noble metals can be utilized (i.e., gold, silver, platinum, palladium, iridium, ruthenium, osmium), either alone or in combination, palladium is particularly desirable. Typically, the amount of noble metal present in the catalyst will be in the range of from 0.01 to 20 weight percent, preferably 0.1 to 5 weight percent. The manner in which the noble metal is incorporated into the catalyst is not considered to be particularly critical. For example, the noble metal may be supported on the zeolite by impregnation means or the like or first supported on another substance such as silica, alumina, activated carbon or the like and then physically mixed with the zeolite. Alternatively, the noble metal can be incorporated into the zeolite by ion-exchange with, for example, Pd tetraammine chloride with or without added ammonium hydroxide. The catalyst is recovered by filtration and washing and is substantially free (<0.1 wt. %) of halide. There are no particular restrictions regarding the choice of noble metal compound or complex used as the source of the noble metal. For example, suitable compounds for such purpose include the nitrates, sulfates, halides (e.g., chlorides, bromides), carboxylates (e.g., acetate), and amine complexes of noble metals. Similarly, the oxidation state of the noble metal is not considered critical. In the case of palladium for instance, the palladium may be in an oxidation state anywhere from 0 to +4 or any combination of such oxidation states. To achieve the desired oxidation state or combination of oxidation states, the noble metal compound after being introduced into the catalyst may be fully or partially pre-reduced. Satisfactory catalytic performance can, however, be attained without any pre-reduction whatsoever. To achieve the active state of palladium, the catalyst may undergo pretreatment such as thermal treatment in nitrogen, vacuum, hydrogen or air.

The catalyst may additionally comprise a binder or the like and may be molded, spray dried, shaped or extruded into any desired form prior to use in epoxidation. In addition to the noble metal, the catalyst may be modified with additional elements such as, for example, lanthanide metals (e.g., europium), iron, cobalt, nickel, boron, aluminum, phosphorus, calcium, vanadium, chromium, manganese, copper, zinc, gallium or zirconium.

Suitable catalysts for use in the process of this invention as well as methods for their preparation are described in more detail in the following published patent applications, each of which is incorporated herein by reference in its entirety: U.S. Pat. No. 5,859,265, JP 4-352771, WO 97/31711, DE 19600709, WO 96/02323, WO 97/47386, WO 97/25143, JP H8-269030 and JP H8-269029.

The aforedescribed catalyst is used in accordance with the invention in combination with a nitrogen compound modifier. Although the precise mechanism by which the modifier operates is not known, these compounds when present during epoxidation usually have the beneficial effect of suppressing the undesirable hydrogenation of the olefin to its saturated hydrocarbon counterpart and thereby greatly improving the selectivity to the desired epoxide. A special advantage of the use of nitrogen containing modifiers such as ammonia and ammonium compounds is that the production of propylene oxide is substantially enhanced. That is, usually not only is the reaction more selective by virtue of a reduction in propane production but in absolute terms propylene oxide formation is improved.

General classes of modifiers suitable for use include amines, amine oxides and especially ammonia and ammonium compounds. Ammonia may be used as a gas, with mixtures of gases. Ammonium hydroxide can be used especially in solvents such as water and methanol. Other amine compounds which can be used are hydroxyl amine and alkyl and aryl hydroxyl amines, hydrazine and alkyl, aryl hydrazines, ammonium salts including ammonium chloride and ammonium bromide, ammonium hydrogen phosphate and diammonium hydrogen phosphate, ammonium acetate and other carboxylates including ammonium trifluoroacetate, aminoacids such as glycine, alanine, phenylalanine and aminomethylphosphonic acid, alkyl amines such as methyl amine, trimethyl amine and trimethyl amine oxide, trialkyl amines in general (ie triethyl and tributyl amines), diamines such as ethylene diamine and substituted (alkyl, aryl) ethylene diamines, ethanolamines, heterocyclic amines, cyclooctyl amine, cyclododecyl amine and alkylated derivatives such as methyl, cyclooctyl amine, 1,4,7-triazacyclononane and 1,4,7-trimethyl-1,4,7-triazacyclononane, heterocyclic aromatic amines and their oxides, heterocyclic aromatic diamines such as 2,2'-bypyridine and 4,4'-bypyridine and 1,10-phenanthroline and alkylated derivatives 2,9-dimethyl-1,10-phenanthroline (neocuprine) and 2.9-dichloro-1,10-phenanthroline and 2,9-dimethyl-4,7-diphenyl-1,10-phenanthroline, 2,2,6,6-tetramethyl-1-piperidinyloxy (Tempo), ditertbutylamine oxide, triazines (including halo and alkyl derivatives thereof)
N,N-dialkyl anilines (including cyano, halo and alkyl derivatives thereof)
halo-N,N-dialkyl anilines
alkyl-N,N-dialkyl anilines
alkyl dimethyl amines (esp. where alkyl=$C_1$–$C_{18}$ hydrocarbon)
phenyl pyridines
2 or 4 dimethylamino pyridines (including alkyl and halo derivatives thereof)
1-alkyl imidazoles (including alkyl and halo derivatives thereof)
1-alkyl piperidines
1-alkyl morpholines
and oxides thereof. Mixtures of tertiary amines and tertiary amine oxides may be utilized. Illustrative tertiary amines and oxides thereof which may be utilized in the present process include, but are not limited to the following amines and their corresponding oxides and isomers, analogs and homologs thereof:
pyridine
2-methyl pyridine (2-picoline)
quinoxaline
quinoline
2-methyl pyrazine
3-methyl pyridine (3-picoline)
4-methyl pyridine (4-picoline)
N,N-dimethyl aniline
2,6-lutidine
2,4-lutidine
3,4-lutidine
2,6-diethyl pyridine
2,6-dipropyl pyridine
2-ethyl pyridine
2-propyl pyridine
2,3-diethyl pyrazine
2-methyl quinoline
1,2,5-trimethyl pyrrole
2-methoxypyridine
9-methyl carbazole
phenanthridine
acridine
2,2'-bipyridine
1-methyl indole
pyrimidine
2-fluoropyridine
2-chloropyridine
2-bromopyridine
2-iodopyridine
1,6-difluoropyridine
3-cyanopyridine
1-methyl triazine
1-methyl imidazole
2-dimethyl amino pyridine
1-methyl piperidine.

Other classes of tertiary amines and tertiary amine oxides suitable for use include,
  trimethyl pyridines
  2-halopyridines (chloro, bromo, iodo)
  dihalopyridines (e.g. 2,6-difluoropyridine)
  cyanopyridines (esp. monosubstituted compounds such as 3-cyanopyridine)
  methylpyrimidines
  halopyrimidines
  pyrazines
  1-alkyl triazoles (including halo and alkyl derivatives thereof).

In accordance with the invention the modifier is simply added to the reaction medium in which the epoxidation is being performed. The modifier may be introduced to the reaction medium all at once either prior to or following initiation of epoxidation or may be added in an incremental or continuous manner.

The amount of modifier used is not believed to be particularly critical, but at a minimum should be effective to improve selectivity to the epoxide as compared to the same reaction carried out under similar conditions in the absence of the modifier. The use of large amounts of modifier tends to suppress the epoxidation, beyond a certain level little further improvement in catalytic performance may be realized. Generally speaking, modifier:noble metal molar ratios in the range of from about 100:1 to 0.01:1 (more preferably, from about 50:1 to 0.05:1) are typically suitable.

The olefin to be used can be any organic compound containing at least one site of ethylenic unsaturation (i.e., at least one carbon—carbon double bond). The olefin can be aliphatic, aromatic or cycloaliphatic in character and may have either a linear or branched structure, with the site(s) of ethylenic unsaturation being terminal and/or internal. The olefin preferably contains 2–30 carbon atoms; the process of the invention is particularly suitable for epoxidizing $C_2$–$C_6$ mono-olefins. More than one double bond may be present, as in a diene or triene for example. The olefin may be a hydrocarbon (i.e., contain only carbon and hydrogen atoms) or may contain functional groups such as halide, carboxyl, hydroxyl, ether, sulfide, carbonyl, cyano, nitro, or amino groups or the like.

Typical examples of suitable olefins include ethylene, propylene, 1-butene, cis- and trans-2-butene, isobutene, 1,3-butadiene, pentenes, isoprene, hexenes, octenes, nonenes, decenes, undecenes, dodecenes, cyclopentene, cyclohexene, dicyclopentadiene, vinylcylohexane, vinyl cyclohexene, allyl chloride, allyl alcohol, methallyl chloride, methallyl alcohol, alkyl acrylates and methacrylates, unsaturated fatty acids and esters thereof, styrene, -methylstyrene, divinylbenzene, indene and stilbene. Mixtures of olefins may, of course, be utilized if so desired. The process of this invention is especially useful for converting propylene to propylene oxide.

The process of the invention may be suitably conducted under the reaction conditions (e.g., temperature, pressure, reactant ratios) described in the following published patent applications, provided the necessary modifier previously described herein is present while the olefin, hydrogen and oxygen are being contacted with the catalyst: WO 96/02323, WO 97/25143, DE 19600709, WO 97/31711, WO 97/47386, JP 4-352771, JP H8-269029, and H8-269030.

The amount of catalyst used may be determined on the basis of the molar ratio of the titanium contained in the titanium zeolite to the olefin that is supplied per unit of time. Typically, sufficient catalyst is present to provide a titanium/olefin feed ratio of from 0.00001 to 0.1. The time required for the epoxidation may be determined on the basis of the gas hourly space velocity, i.e., the total volume of olefin, hydrogen, oxygen and carrier gas(es) per hour per unit of catalyst volume (abbreviated as GHSV). A GHSV in the range of 10 to 10,000 $hr^{-1}$ is typically satisfactory.

Depending on the olefin to be reacted, the epoxidation according to the invention can be carried out in the liquid phase, the gas phase, or in the supercritical phase. When a liquid reaction medium is used, the catalyst is preferably in the form of a suspension or fixed-bed. The process may be performed using a continuous flow, semi-batch or batch mode of operation.

If epoxidation is carried out in the liquid phase, it is advantageous to work at a pressure of 1–100 bars and in the presence of one or more solvents. Suitable solvents include, but are not limited to, lower aliphatic alcohols such as methanol, ethanol, isopropanol, and tert-butanol, or mixtures thereof, and water. Fluorinated alcohols can be used. It is also possible to use mixtures of the cited alcohols with water.

Epoxidation according to the invention is carried out at a temperature effective to achieve the desired olefin epoxidation, preferably at temperatures in the range of 0–125° C. (more preferably, 20–80° C.). The molar ratio of hydrogen to oxygen can usually be varied in the range of $H_2:O_2$=1:10 to 5:1 and is especially favorable at 1:5 to 2:1. The molar ratio of oxygen to olefin is usually 1:1 to 1:20, and preferably 1:1.5 to 1:10. Relatively high $O_2$ to olefin molar ratios (e.g., 1:1 to 1:3) may be advantageous for certain olefins. As the carrier gas, any desired inert gas can be used. The molar ratio of olefin to carrier gas is then usually in the range of 1:100 to 4:1, and especially 1:20 to 1:1.

As the inert carrier gas, noble gases such as helium, neon, argon, krypton, and xenon are suitable in addition to nitrogen and carbon dioxide. Saturated hydrocarbons with 1–8, especially 1–6, and preferably with 1–4 carbon atoms, e.g., methane, ethane, propane and n-butane, are also suitable. Nitrogen and saturated $C_1$–$C_4$ hydrocarbons are the preferred inert carrier gases. Mixtures of the listed inert carrier gases can also be used.

Specifically in the epoxidation of propylene according to the invention, propane can be supplied in such a way that, in the presence of an appropriate excess of carrier gas, the explosive limits of mixtures of propylene, propane, hydrogen, and oxygen are safely avoided and thus no explosive mixture can form in the reactor or in the feed and discharge lines.

The productivity of spent or partially spent catalysts can be enhanced at least in part by treatment with ammonia or ammonium hydroxide. In that practice of the invention wherein ammonium hydroxide is perodically or continuously added to the reaction zone, this addition effectively regenerates the catalyst in situ thus avodiing at least to some extent catalyst activity decline.

A series of experiments were carried out for the conversion of propylene to propylene oxide in accordance with the invention. In each case, the reaction was carried out in a glass reactor at 3 psig with a Teflon coated stirring bar (1000 rpm) with the solvents and temperatures listed in the Table. Gas flow rate into the reactor was 25.1 cc/min propylene/hydrogen (20 vol % hydrogen) and 88.0 cc/min nitrogen/oxygen/methane (by volume 5% 02, 0.6% methane, balance nitrogen). A solvent containing vaporizer was placed in the feed line to prevent evaporative loss of the reactor solvent. In all cases 3 grams of catalyst were used. In the water run, 130 grams of water was the solvent. In the methanol/water runs, 112 grams of methanol/water (3/1 by wt) was used. Reactor effluents were analyzed directly by on-line gas chromatography.

Catalysts employed were prepared as follows:

Catalyst A

Palladium tetraammine nitrate (7.77 grams) was dissolved in 310 grams of 25 wt % aqueous ammonium hydroxide, stirred at 23° C. for 3 days and filtered.

In a single-neck round-bottom flask 15 grams of TS-1 titanium silicalite (2.1 wt % titanium, calcined at 550° C. in air for 4 hrs) was slurried in 60 grams of deionized water. To this slurry, 7.1 grams of the above solution was added and heated at 80° C. under a nitrogen atmosphere for 24 hrs. The liquid was removed by rotoevaporation at 50° C. The solids were dried in a vacuum oven at 60° C. for 24 hrs. The dried solids were calcined in an oven under a nitrogen atmosphere at 150° C. for 4 hrs. The catalyst contained about 0.5 wt % Pd.

Catalyst B

Palladium tetraammine nitrate (7.77 grams) was dissolved in 310 grams of 25 wt % aqueous ammonium hydroxide, stirred at 23° C. for 3 days and filtered.

In a single-neck round-bottom flask 15 grams of TS-1 titanium silicalite (1.2 wt % titanium, calcined at 550° C. in air for 4 hrs) was slurried in 60 grams of deionized water. To this slurry, 7.1 grams of the above solution was added and heated at 80° C. under a nitrogen atmosphere for 24 hrs. The liquid was removed by rotoevaporation at 50° C. The solids were dried in a vacuum oven at 60° C for 24 hrs.

(1.2 wt % titanium, calcined in air at 550° C.) and 100 grams of deionized water. Palladium dibromide (0.095 gram) was dissolved in 15 grams of 30 wt % ammonium hydroxide and added to the silicalite slurry over a 10 minute period. The reaction mixture was allowed to stir at 23° C. for 2 hrs. The liquid was removed by rotoevaporation at 50° C. The solids were dried in a vacuum oven at 50° C. for 4 hrs. The dried solids were then transferred to a glass tube and treated with nitrogen (100 cc/min) at 150° C. for 4 hrs. The catalyst contained about 0.12wt % Pd.

The results obtained are given in the following Table 1.

TABLE 1

| RUN NUMBER | CATALYST | TEMP ° C. | SOLVENT | VOL % PO BEFORE AMINE | VOL % PO AFTER AMINE | % H2/O2 CONV. BEFORE AMINE | % H2/O2 CONV. AFTER AMINE |
|---|---|---|---|---|---|---|---|
| 1 | A | 60 | Water | 0.058 | 0.18[1] | 65/36 | 28/20 |
| 2 | B | 45 | Methyl Alcohol/Water (3/1 wt) | 0.008 | 0.098[2] | 68/34 | 28/20 |
| 3 | C | 45 | Methyl Alcohol/Water (3/1 wt) | 0.14 | 0.2[3] | 38/20 | 15/10 |
| 4 | B | 45 | Methyl Alcohol/Water (3/1 wt) | see[4] | 0.2 | NA | 40/20 |
| 5 | B | 45 | Methyl Alcohol/Water (3/1 wt) | 0.2 | 0.24[5] | 40/20 | 40/20 |
| 6 | D | 45 | Methyl Alcohol/Water (3/1 wt) | 0.18 | 0.26[6] | 40/15 | 25/15 |

Footnotes to Table 1
1. Added 0.52 grams of 30% aqueous ammonium hydroxide mixed with 0.54 grams of deionized water.
2. Added 0.5 grams of 30% aqueous ammonium hydroxide mixed with 0.5 grams of deionized water. At the time of the ammonium hydroxide addition, the catalyst was also producing methyl formate (0.2 vol %) and a large amount of propane (0.8 vol %) in the vapor. After the ammonium hydroxide addition, the methyl formate in the vapor was reduced to 0 vol % and the propane reduced to 0.01 vol %.
3. Added 0.2 grams of 30% aqueous ammonium hydroxide mixed with 1.0 gram of deionized water and 4 grams of methanol. At the time of the ammonium hydroxide addition the catalyst was also producing 0.16 vol % propane in the vapor. After the ammonium hydroxide addition, the propane in the vapor was reduced to 0.03 vol %.
4. The catalyst slurry in the reactor was treated with 0.6 grams of 30% aqueous ammonium hydroxide and allowed to stir in air for 1 hr at 23° C. before the feed gases were introduced.
5. Added 25 milligrams of ammonium bromide dissolved in 2 grams of deionized water mixed with 20 grams of methanol. At the time of the ammonium bromide addition the catalyst was producing methyl formate (0.2 vol %) in the vapor, after the addition of ammonium bromide the methyl formate dropped to 0 vol %. However, the addition of ammonium bromide caused the propane to increase from 0.08% to 0.22 vol %.
6. Added 0.1 gram of 30% aqueous ammonium hydroxide dissolved in 25 grams of methanol. At the time of the ammonium hydroxide addition, the catalyst was producing 0.56 vol % propane in the vapor. After the addition of ammonium hydroxide the propane in the vapor was reduced to 0.18 vol %.

These solids were then calcined in an oven in air at 450° C. for 16 hrs. The solids were then transferred to a glass tube and treated with 5% hydrogen in nitrogen (100 cc/min) at 100° C. for 4 hrs. The catalyst contained about 0.5 wt % Pd.

Catalyst C

An Erlenmeyer flask equipped with a Teflon coated stir bar was charged with 30 grams of TS-1 titanium silicalite (1.2 wt % titanium, calcined in air at 550° C.) and 100 grams of deionized water. Tetraammine palladium dinitrate (0.45 grams) was dissolved in 15 grams of 30 wt % ammonium hydroxide and added to the silicalite slurry over a 15 minute period. The reaction mixture was allowed to stir at 23° C. for 1 hr. The liquid was removed by rotoevaporation at 50° C. The solids were dried in a vacuum oven at 50° C. for 4 hrs. The dried solids were then transferred to a glass tube and treated with nitrogen (100 cc/min) at 150° C. for 4 hrs. The catalyst contained about 0.5 wt % Pd.

Catalyst D

An Erlenmeyer flask equipped with a Teflon coated stir bar was charged with 30 grams of TS-1 titanium silicalite As can be seen from the above, the use of the nitrogen compound modifier sharply increased the production of the desired propylene oxide product.

It can also be seen that practice of the invention also shows an advantage in $H_2$ and $O_2$ conversion. More propylene oxide is made but less $O_2$ and $H_2$ is consumed. This is an improvement in $H_2$ and $O_2$ utilization which is very significant for process economics.

We claim:
1. A process for producing an epoxide comprising reacting an olefin, hydrogen and oxygen in the presence of (a) a catalyst comprised of a titanium or vanadium zeolite and a noble metal and (b) a nitrogen-compound modifier at a temperature effective to form the epoxide corresponding to the olefin.
2. The process of claim 1 wherein the modifier is ammonia or an ammonium compound.
3. The process of claim 1 wherein the modifier is ammonium hydroxide.
4. The process of claim 1 wherein the titanium zeolite is titanium silicalite.
5. The process of claim 1 wherein the olefin is a $C_2$–$C_6$ mono-olefin.

6. The process of claim 1 wherein the noble metal is palladium.

7. A process for producing an epoxide comprising reacting a $C_2$–$C_6$ mono-olefin, hydrogen and oxygen in the presence of (a) a catalyst comprised of titanium silicalite and palladium and (b) a nitrogen-compound modifier at a temperature of from 20° C. to 80° C. to form the epoxide corresponding to the $C_2$–$C_6$ mono-olefin.

8. The process of claim 7 wherein the modifier is ammonia or an ammonium compound.

9. The process of claim 7 wherein the $C_2$–$C_6$ mono-olefin is propylene.

10. The process of claim 7 wherein the titanium silicalite is TS-1.

11. The process of claim 7 wherein said reacting is carried out in a liquid medium.

12. The process of claim 11 wherein the liquid medium is comprised of methanol, water or mixtures of methanol and water.

13. The process of claim 11 wherein the modifier is introduced into said liquid medium.

14. The process of claim 6 wherein the catalyst is comprised of from 0.1 to 5.0 weight percent Pd.

15. The process of claim 6 wherein the molar ratio of modifier:noble metal is in the range of from 50:1 to 0.05:1.

16. The process of claim 8 wherein the modifier is added continuously to the reaction system.

17. The process of claim 8 wherein the modifier is ammonium chloride, ammonium bromide, ammonium dihydrogen phosphate, diammonium hydrogen phosphate, ammonium acetate, or mixtures thereof.

* * * * *